United States Patent
Ma et al.

(10) Patent No.: US 10,620,123 B2
(45) Date of Patent: Apr. 14, 2020

(54) FLUORESCENCE DETECTION INSTRUMENT

(71) Applicant: Delta Electronics Int'l (Singapore) Pte Ltd, Singapore (SG)

(72) Inventors: Bo Ma, Singapore (SG); Jei-Yin Yiu, Singapore (SG); Song-Bin Huang, Singapore (SG); Po-Yao Huang, Singapore (SG); Chun-Jung Li, Singapore (SG); Yu-Kai Kao, Singapore (SG)

(73) Assignee: DELTA ELECTRONICS INT'L (SINGAPORE) PTE LTD, Singapore (SG)

( * ) Notice: Subject to any disclaimer, the term of this patent is extended or adjusted under 35 U.S.C. 154(b) by 246 days.

(21) Appl. No.: 15/909,069

(22) Filed: Mar. 1, 2018

(65) Prior Publication Data

US 2019/0242822 A1   Aug. 8, 2019

(30) Foreign Application Priority Data

Feb. 8, 2018   (SG) .............................. 10201801098P

(51) Int. Cl.
*G01N 1/00* (2006.01)
*G01N 21/64* (2006.01)
(Continued)

(52) U.S. Cl.
CPC ............ *G01N 21/6428* (2013.01); *B01L 7/52* (2013.01); *C12Q 1/686* (2013.01); *C12Q 1/6851* (2013.01); *G01N 21/0332* (2013.01); *G01N 21/645* (2013.01); *B01L 9/06* (2013.01); *B01L 2300/0654* (2013.01);
(Continued)

(58) Field of Classification Search
CPC ........................................................ G01N 1/00
See application file for complete search history.

(56) References Cited

U.S. PATENT DOCUMENTS

2009/0298129 A1*  12/2009  Spence .................. B01L 3/021
                                                                        435/91.2

FOREIGN PATENT DOCUMENTS

| CN | 104245915 A | 12/2014 |
| CN | 106754343 B | 10/2017 |
| TW | 201741450 A | 12/2017 |

* cited by examiner

*Primary Examiner* — Jyoti Nagpaul
(74) *Attorney, Agent, or Firm* — Kirton McConkie; Evan R. Witt

(57) ABSTRACT

The disclosure relates to a fluorescence detection instrument, including a base, a heating module, a detecting module, an illumination module, and an actuation module. The heating module, the detecting module, and the actuation module are disposed on the base. The heating module includes plural heating holders, wherein each of the plural heating holders is adapted to accommodate a light-transmissive reaction container adapted to contain a fluorescent reaction mixture with at least one targeted fluorescent probe respectively. The detecting module is configured with the heating module to form plural detection channels, wherein the plural heating holders are located at the plural detection channels respectively. The actuation module is connected with the illumination module and adapted to drive the illumination module to move to at least one predetermined position to selectively match at least one combination of the heating holder on the corresponding detection channel.

23 Claims, 15 Drawing Sheets

(51) Int. Cl.
  *C12Q 1/686* (2018.01)
  *C12Q 1/6851* (2018.01)
  *B01L 7/00* (2006.01)
  *G01N 21/03* (2006.01)
  *B01L 9/06* (2006.01)
(52) U.S. Cl.
  CPC .................. *B01L 2300/0681* (2013.01); *B01L 2300/1838* (2013.01); *G01N 2021/6417* (2013.01); *G01N 2021/6439* (2013.01); *G01N 2201/0407* (2013.01); *G01N 2201/068* (2013.01)

FLUORESCENCE DETECTION INSTRUMENT

FIELD OF THE INVENTION

The present invention relates to a fluorescence detection instrument, and more particularly to a fluorescence detection instrument with high signal-to-noise ratio for multiplexing qPCR application.

BACKGROUND OF THE INVENTION

The demand of acquiring large amounts of a specific segment of DNA efficiently for different purposes is booming in recent years. Among the entire existing DNA sequencing techniques, Polymerase Chain Reactions (PCR) is one of the most economical and straightforward techniques amplifying billion copies of targeted DNA segments in short period of time. The applications of PCR technique are broadly adopted, such as selective DNA isolation for genetic identification, forensic analysis for analyzing ancient DNA in archeology, medical applications for genetic testing and tissue typing, fast and specific diagnosis of infectious diseases for hospitals and research institutes, inspection of environmental hazards for food safety, genetic identification for investigating criminals, and so on. For PCR technique, only small amount of DNA samples are required from blood or tissues. By utilizing a fluorescent probe into the nucleic acids solutions, the amplified DNA segments could be detected through the help of fluorescent molecules.

To simultaneously detect and analyze the presence of targeted nucleic acids in a batch of biological samples, fluorescent dyes detection technique is usually applied. After the light source at specific wavelength illuminates on the targeted nucleic acids, the DNA-binding fluorescent probes of the nucleic acids will react and enable fluorescent signals to be emitted. The fluorescent signal is an indication of the existence of the targeted nucleic acids. This technique has been employed for the novel PCR technique, which is called real time quantitative PCR or qPCR. qPCR is the early-phase PCR detection with higher sensitivity and better precision than the conventional PCR technique which is an end-point PCR detection. An optical device is essential to detect the fluorescent light emitted from the specific nucleic acids segments for qPCR technique. The optical device has to provide a light source to excite the fluorescent probe at their specific wavelengths, and in the meanwhile, it detects the fluorescent signals emitted from the fluorescent probe.

There are a large number of fluorescent detection instruments known in the art that are employed to image fluorescence signals, but the bulky size and weight of such instruments are huge and the signal-to-noise ratio (SNR) thereof cannot meet the practical requirements. On the other hand, another problem that all fluorescence detection instruments have in common is the huge intensity difference between the excitation light and the fluorescence light signal. If at least one fluorescent probe is involved in the multiplexing, to isolate different excitation and fluorescence signals become a very important task. In general, different excitation filters are required when multiple fluorescent probes are present in a sample. Each excitation filter is able to transfer at least one excitation light at specific wavelengths from the light source to the assembly of multiple individual sites. A large number of expensive optical devices have to be employed with respect to different excitation filters, respectively. While a sample including multi fluorescent probes, the sample has to be placed in several different sites for detecting sequentially. It is not convenient and the detection result will be influenced due to the temperature and reaction time changes.

In light with the requirements and the issues addressed above, there is a need of providing an improved fluorescence detection instrument with high signal-to-noise ratio for multiplexing qPCR application.

SUMMARY OF THE INVENTION

An object of the present invention is to provide a fluorescence detection instrument with high signal-to-noise ratio for minimizing the size and the weight of the instrument, and still providing superior performance for multiplexing qPCR application with affordable cost.

According to an embodiment of the present invention, there is a fluorescence detection instrument including a base, a heating module, a detecting module, an illumination module, and an actuation module. The heating module is disposed on the base and includes plural heating holders. Each of the plural heating holders is adapted for accommodating a light-transmissive reaction container adapted to contain a fluorescent reaction mixture with at least one targeted fluorescent probe, respectively. The detecting module is disposed on the base and configured with the heating module to form plural detection channels. The plural heating holders are located on the plural detection channels, respectively. The actuation module is disposed on the base, connected with the illumination module and adapted to drive the illumination module to move to at least one predetermined position to selectively match at least one combination of the heating holder on the corresponding detection channel.

In an embodiment, the illumination module includes plural light sources and plural first filters, wherein the plural light sources are disposed relative to the plural first filters, respectively, and the light source and the first filter are configured to form a first optical axis.

In an embodiment, the plural light sources includes at least one of a single color LED, a laser diode, a mercury lamp, and a halogen light bulb.

In an embodiment, the illumination module includes plural second filters relative to the plural first filters respectively, wherein the plural second filters are located between the detecting module and the heating module.

In an embodiment, the plural first filters and the plural second filters include single band pass filters.

In an embodiment, the plural first filters include excitation filters, and the plural second filter include emission filters.

In an embodiment, the detecting module includes plural detectors and plural optic sets, wherein the plural detectors are disposed relative to the plural optic sets respectively, and the detector and the corresponding plural optic set are configured to form a second optical axis along the corresponding detection channel.

In an embodiment, the detector includes at least one of a silicon photodiode, a photomultiplier tube, a charged-couple device, a complementary metal-oxide semiconductor, and an avalanche photodiode.

In an embodiment, each of the plural optic sets includes at least one condensing optic located nearby the heating module and at least one imaging optic located nearby the corresponding detector.

In an embodiment, each of the plural optic sets includes an emission filter disposed between the condensing optic and the imaging optic.

In an embodiment, each of the plural heating holders includes a heating chamber, a first optical aperture, and a second optical aperture, wherein the first optical aperture and the second optical aperture are in communication with each other through the heating chamber, and the second optical aperture is located at the corresponding second optical axis.

In an embodiment, the diameter of the second optical aperture is ranged from 1 mm to 2.5 mm, and the diameter of the first optical aperture is ranged from 2 mm to 3 mm.

In an embodiment, while the illumination module is matched and aligned to the heating holder on the corresponding detection channel, the first optical axis is crossed with the corresponding second optical axis in the heating chamber through the first optical aperture and the second optical aperture respectively.

In an embodiment, while the first optical axis and the corresponding second optical axis are crossed in the heating chamber through the first optical aperture and the second optical aperture respectively, the corresponding second optical axis is tilted from the first optical axis at an angle ranged from 2 degrees to 12 degrees.

In an embodiment, the heating module further includes a heater connected with the plural heating holders.

In an embodiment, the heater includes a thermoelectric cooling heater for thermal cycling control.

In an embodiment, the heating module further includes a heat sink connected to the heater.

In an embodiment, the actuation module includes at least one actuator, wherein the actuator includes at least one of a rotary actuator driven by fluid or vacuum pressure, a piezoelectric (PZT) actuator, an electro-actuated polymer (EAP) actuator, and an electromagnetic motor.

In an embodiment, the actuation module includes a moveable support rack, wherein the illumination module is disposed on the moveable support rack and connected to the at least one actuator, wherein the at least one actuator is configured to drive the movable support rack and move the illumination module to selectively match the at least one combination of the heating holder on the corresponding detection channel.

In an embodiment, the actuation module includes a gear module and at least one guiding rail module, wherein the gear module is disposed between and connected with the actuator and the movable support rack, and the at least one guiding rail module is disposed between and connected with the moveable support rack and the base.

In an embodiment, the fluorescence detection instrument further includes a movable support rack, wherein the illumination module is disposed on the moveable support rack and connected to the actuation module, wherein the actuation module is configured to drive the movable support rack and move the illumination module to selectively match the at least one combination of the heating holder on the corresponding detection channel.

In an embodiment, the number of the combinations of the illumination module and the heating holder on the corresponding detection channel is less than the total number of the plural detection channels.

In an embodiment, the plural light sources include at least two adjacent light sources adapted to provide the same color of light.

In an embodiment, the plural light sources include at least two adjacent light sources adapted to provide the different colors of light.

In an embodiment, the plural light sources include at least two adjacent light sources adapted to provide the same color of light and at least two adjacent light sources adapted to provide the different colors of light, wherein the at least two adjacent light sources adapted to provide the same color of light are disposed at an end of the arrangement of the plural light sources.

The above objects and advantages of the present invention become more readily apparent to those ordinarily skilled in the art after reviewing the following detailed description and accompanying drawings, in which:

DETAILED DESCRIPTION OF THE PREFERRED EMBODIMENT

Figure 1:
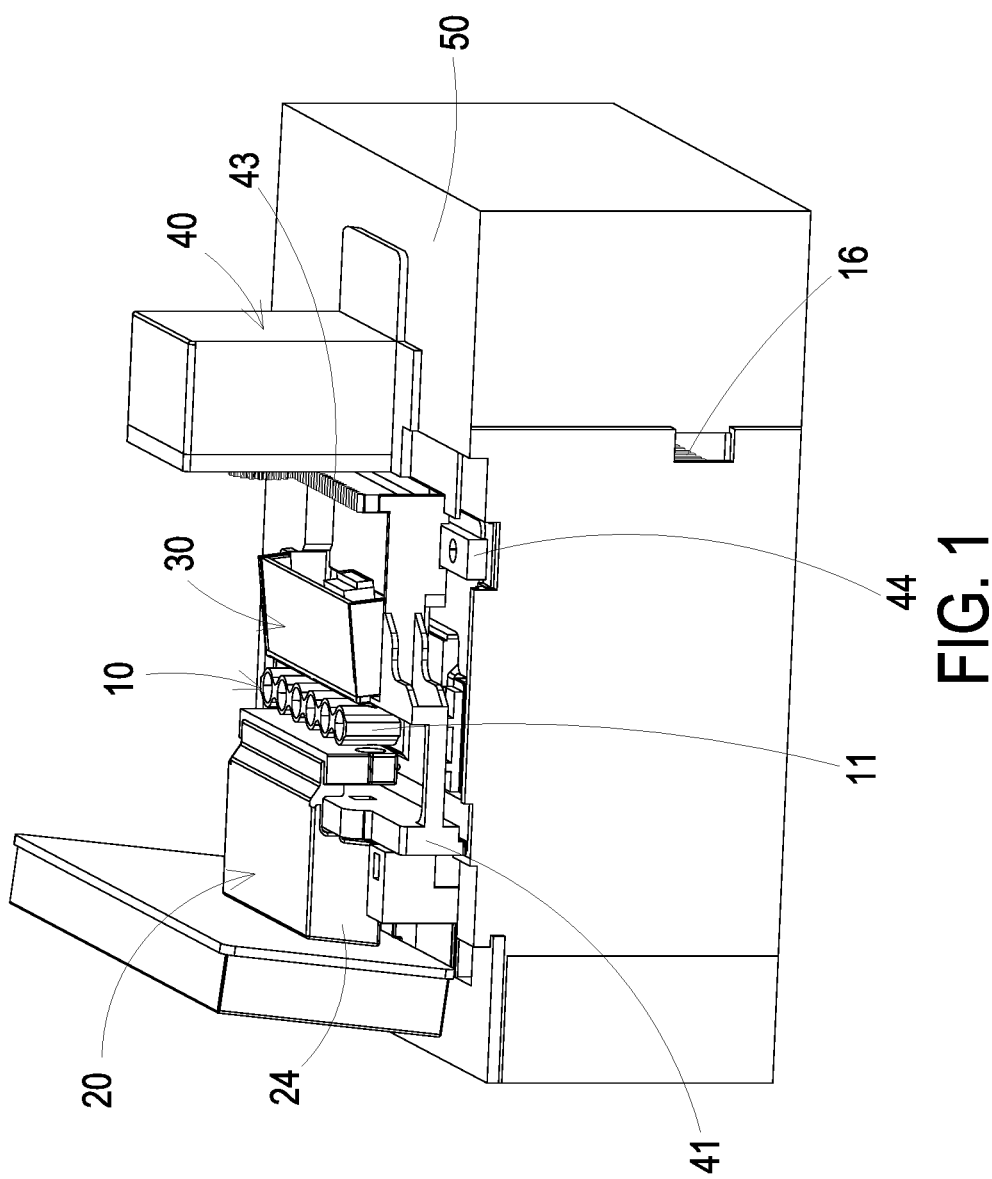
FIG. 1 shows a schematic view of the fluorescence detection instrument according to an embodiment of the present invention.

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed. Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly. When an element is referred to as being "connected," or "coupled," to another element, it can be directly connected or coupled to the other element or intervening elements may be present. Although the wide numerical ranges and parameters of the present disclosure are approximations, numerical values are set forth in the specific examples as precisely as possible. In addition, although the "first," "second," "third," and the like terms in the claims be used to describe the various elements can be appreciated, these elements should not be limited by these terms, and these elements are described in the respective embodiments are used to express the different reference numerals, these terms are only used to distinguish one element from another element. For example, a first element could be termed a second element, and, similarly, a second element could be termed a first element, without departing from the scope of example embodiments. Besides, "and/or" and the like may be used herein for including any or all combinations of one or more of the associated listed items. While the numerical ranges and parameters set forth for the broad scope of the present invention are approximations, the numerical value reported in the specific examples set forth as accurately as possible. However, any numerical values inherently contain certain errors necessarily the standard deviation found in the respective testing measurements caused. Also, as used herein, the term "about" generally means away from a given value or a range of 10%, 5%, 1% or 0.5%. Alternatively, the word "about" means within an acceptable standard error of ordinary skill in the art-recognized average. In addition to the operation/working examples, or unless otherwise specifically stated otherwise, in all cases, all of the numerical ranges, amounts, values and percentages, such as the number for the herein disclosed materials, time duration, temperature, operating conditions, the ratio of the amount, and the like, should be understood as the word "about" decorator. Accordingly, unless otherwise indicated, the numerical parameters of the present invention and scope of the appended patent proposed is to follow changes in the desired approximations. At least, the number of significant digits for each numerical parameter should at least be reported and explained by conventional rounding technique is applied. Herein, it can be expressed as a range between from one endpoint to the other or both endpoints. Unless otherwise specified, all ranges disclosed herein are inclusive.

The embodiment of the present invention provides a fluorescence detection instrument, which includes an adjustable optical system selectively illuminating multiple fluorescent samples arranged in linear positions. By changing positions of the illumination module, the fluorescence detection instrument of the embodiment of the present invention could work on a batch of bio-samples with multiple color and achieve the multiplexing qPCR application.

Figure 2:
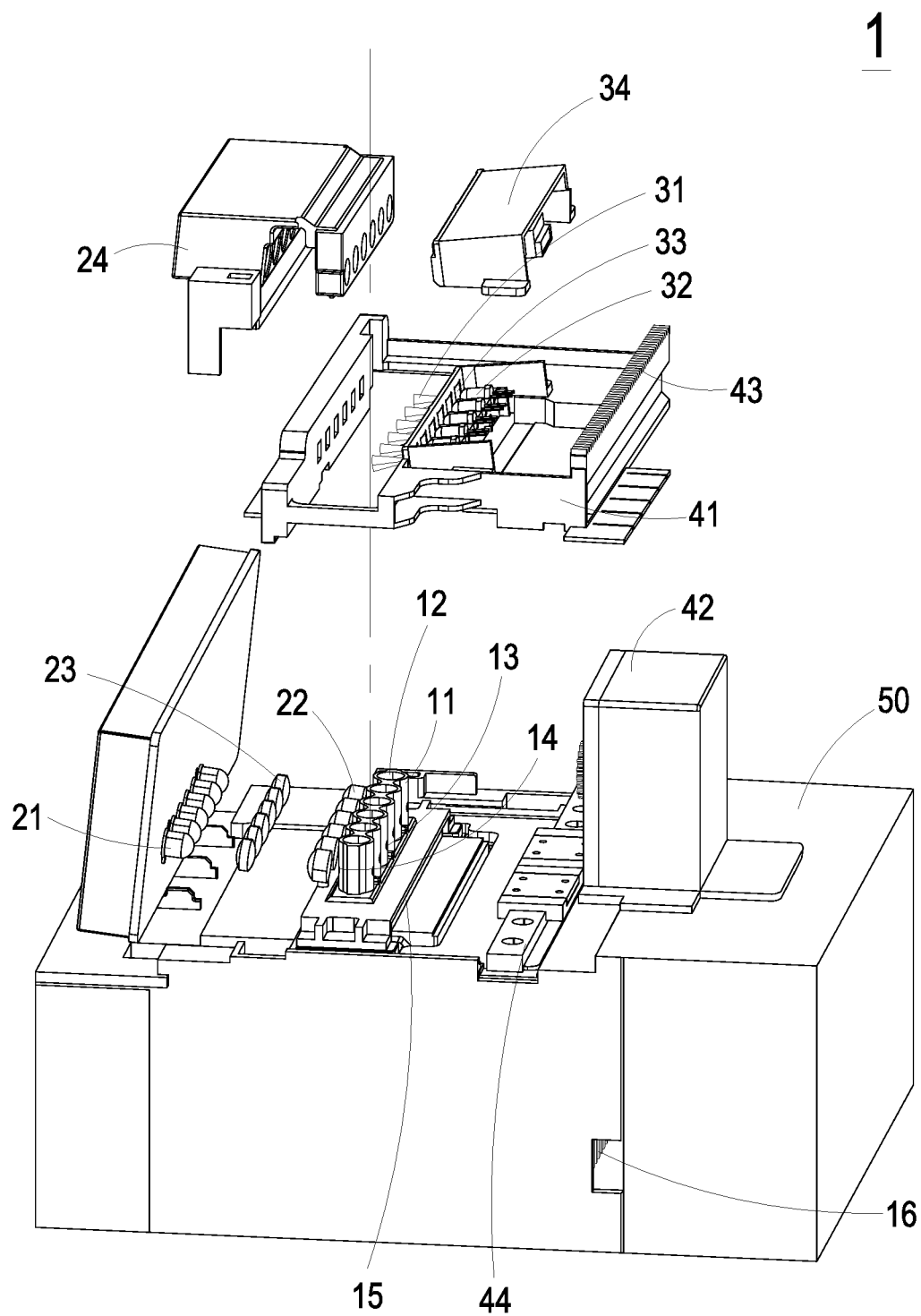
FIG. 2 shows an exploded view of the fluorescence detection instrument of FIG. 1.
Figure 3:
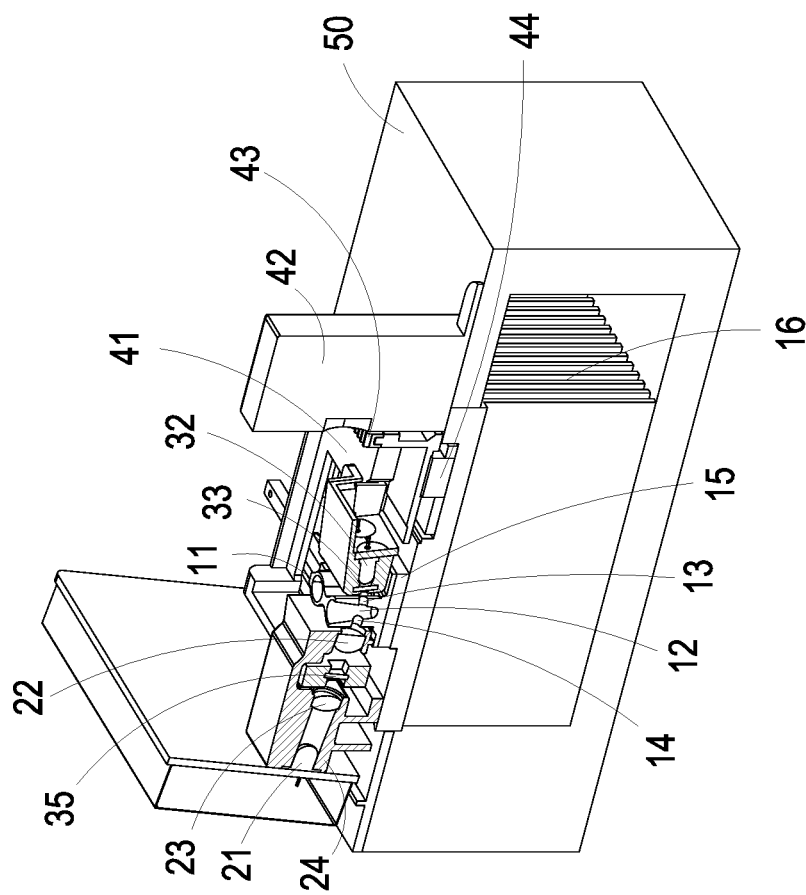
FIG. 3 shows a cross sectional view of the fluorescence detection instrument of FIG. 1.
Figure 4:
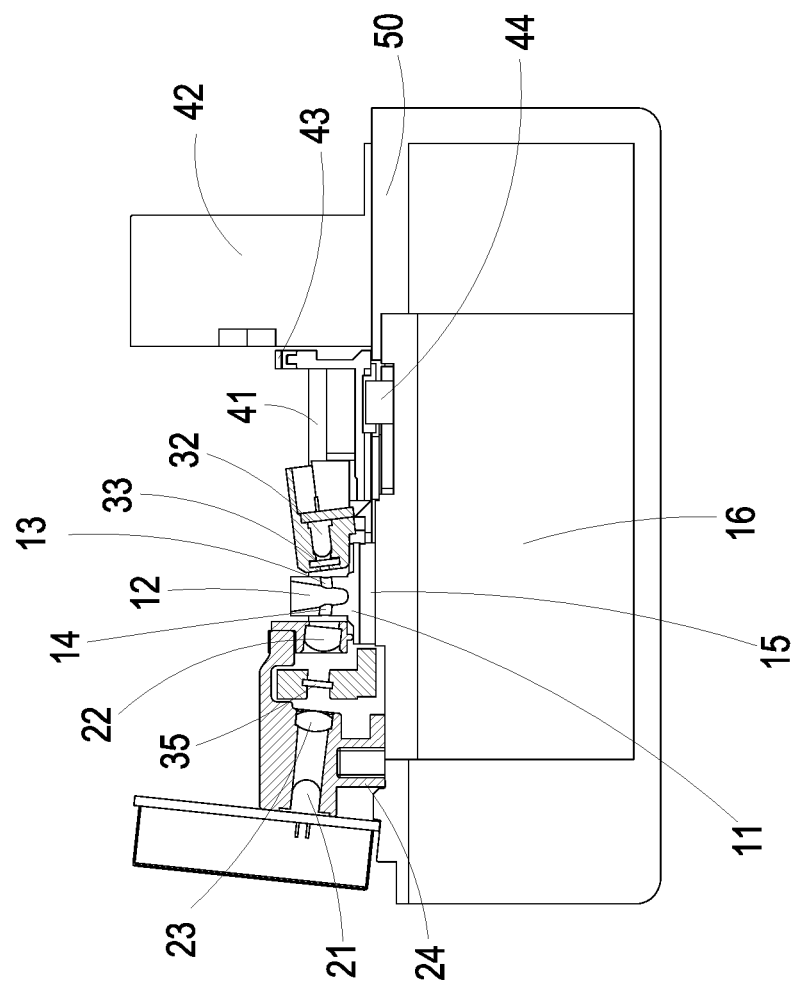
FIG. 4 shows a lateral view of FIG. 3.

Please refer to FIGS. 1 to 4, wherein FIG. 1 shows a schematic view of the fluorescence detection instrument according to an embodiment of the present invention, FIG. 2 shows an exploded view of the fluorescence detection instrument of FIG. 1, FIG. 3 shows a cross-sectional view of the fluorescence detection instrument of FIG. 1, and FIG. 4 shows a lateral view of FIG. 3. As shown in FIGS. 1 to 4, the embodiment of the present invention provides the fluorescence detection instrument 1 including a heating module 10, a detecting module 20, an illumination module 30, an actuation module 40, and a base 50. The heating module 10 is disposed on the base 50 and includes plural heating holders 11. Each of the plural heating holders 11 is adapted for accommodating a light-transmissive reaction container (not shown) adapted to contain a fluorescent reaction mixture with at least one targeted fluorescent probe, respectively. The detecting module 20 is disposed on the base 50 and configured with the heating module 10 to form plural detection channels. The plural heating holders 11 are located on the plural detection channels, respectively. In the embodiment, there are for example six detection channels positioned linearly and provided for multiplexing qPCR application. The six heating holders 11 are located at the front of the six detection channels, respectively. The illumination module 30 is configured to provide plural light sources 32 with light beams at specific wavelengths. In some embodiments, the number of the light sources 32 is equal to or more than the number of the detection channels, but the present invention is not limited thereto. In the embodiment, the illumination module 30 includes for example six sets of light sources 32 and first filters 33, each set of the light source 32 and the first filter 33 is configured to provide the light beam at the specific wavelength. Thus, there are six light beams provided by the illumination module 30 to selectively illuminate the light-transmissive reaction container placed on the heating holders 11 of the detection channels. In the embodiment, the actuation module 40 is connected with the illumination module 30 and adapted to drive the illumination module 30 to move to at least one predetermined position to selectively match at least one combination of the heating holder 11 on the corresponding detection channel. In the embodiment, the light-transmissive reaction container is for example a tube.

Figure 5:
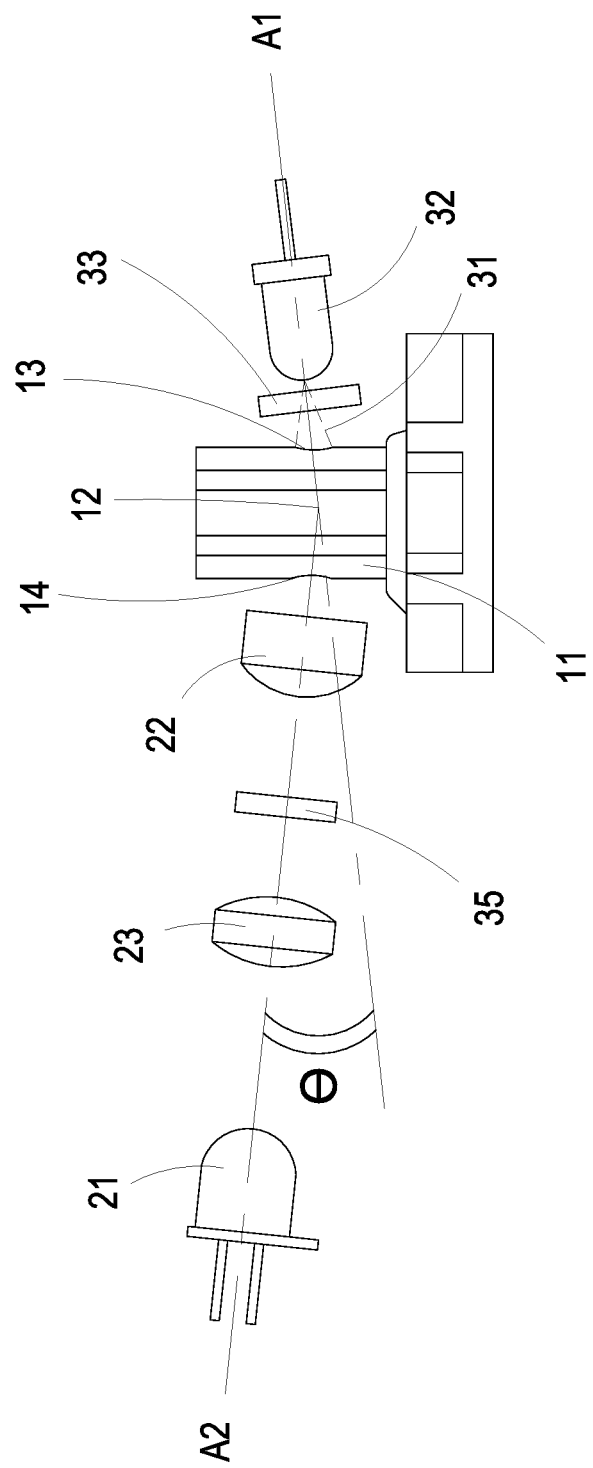
FIG. 5 shows one combination of the illumination module and the heating holder on the corresponding detection channel according to an embodiment of the present invention.

FIG. 5 shows one combination of the light beam and the heating holder on the corresponding detection channel according to an embodiment of the present invention. While the light sources 32 is matched and aligned to the heating holder 11 on the corresponding detection channel, the targeted fluorescent probe of the fluorescent reaction mixture contained in the light-transmissive reaction container accommodated in the heating holder 11 is excited by the light beam of the corresponding light source and a fluorescent light is generated and transmitted to the detecting module 20 along the corresponding detection channel. For selectively matching and aligning the at least one of the plural light source 32 to the at least one of the plural heating holders 11 on the plural detection channels and obtaining at least one combination of the light source 32 and the heating holder 11 on the corresponding detection channel, the illumination module 30 can be driven to slide for example but not limited to a linear displacement by the actuation module 40. It is noted that any actuation module capable of changing the relative positions between the illumination module 30 and the heating module 10 are suitable in the embodiment of the present invention.

In an embodiment, the actuation module 40 further includes a moveable support rack 41, an actuator 42, at least one gear module 43, and the at least one guiding rail module 44. The detecting module 20, the heating module 10, and the actuator 42 of the actuation module 40 are constructed together on the base 50 and disposed in fixed positions. The moveable support rack 41 is connected with the base 50 through the guiding rail module 44 having for example one guiding rail disposed on the base 50 and capable of sliding relative to the base 50. The illumination module 30 is constructed on the moveable support rack 41 and the moveable support rack 41 is connected to the actuator 42 through the gear module 43 disposed thereon. Thus, the actuator 41 and the at least one gear module 43 are engaged with each other and capable of driving the illumination module 30 on the movable support rack 41 to change the position and selectively match at least one combination of the light source 32 and the heating holder 11 on the corresponding detection channel.

In another embodiment, the fluorescence detection instrument 1 further includes a moveable support rack 41. The illumination module 30 is constructed on the moveable support rack 41 and connected to the actuation module 40. The actuation module 40 is configured to drive the movable support rack 41 and move the illumination module 30 to selectively match the at least one combination of the heating holder 11 at the corresponding detection channel.

Figure 6:
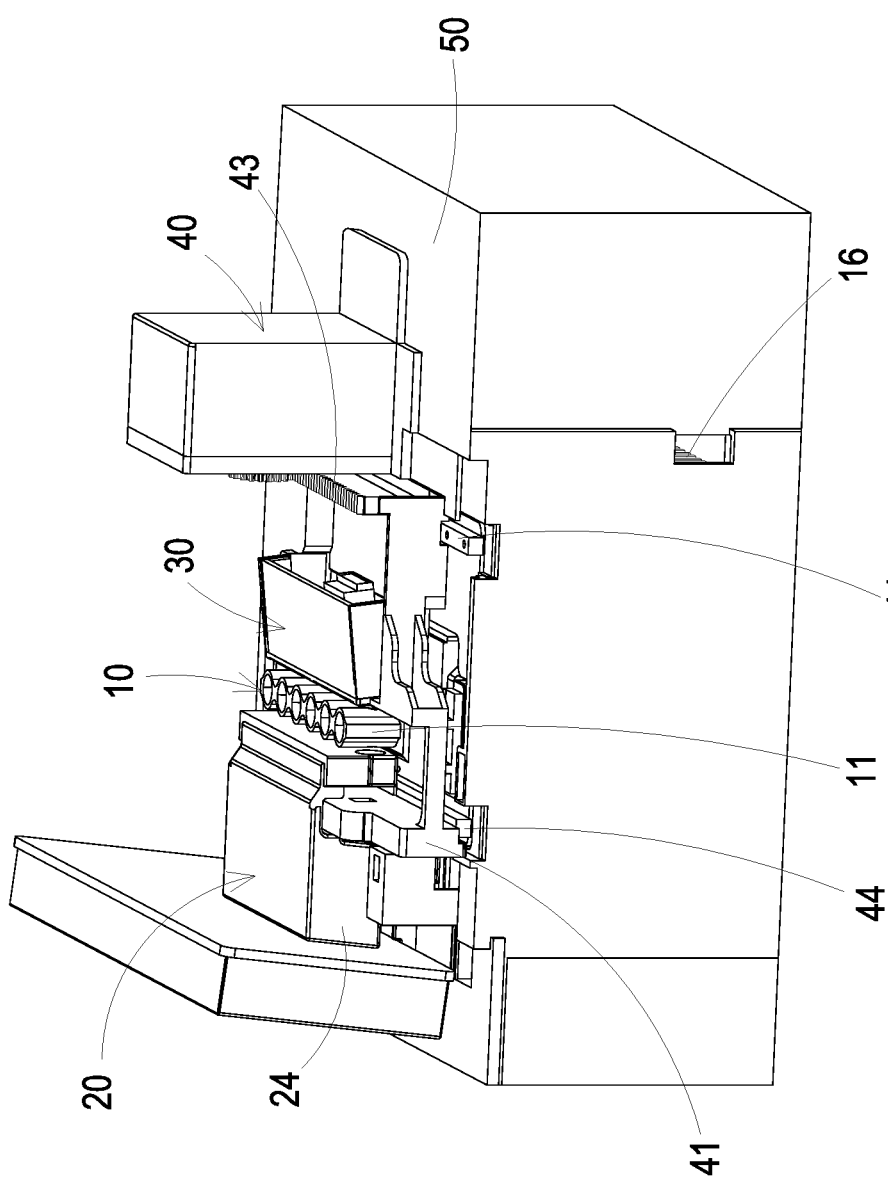
FIG. 6 shows a schematic view of the fluorescence detection instrument according to another embodiment of the present invention.
Figure 7:
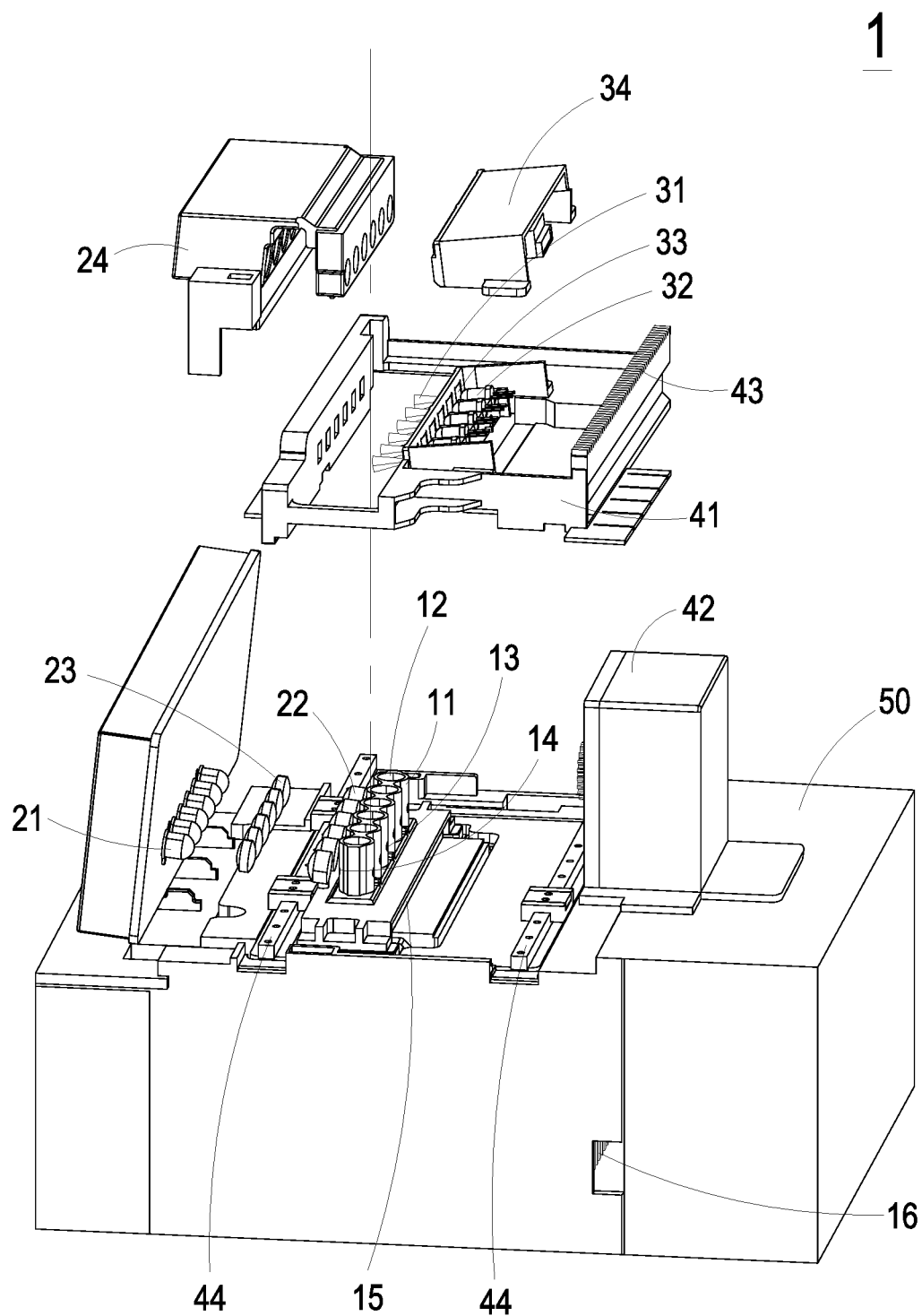
FIG. 7 shows an exploded view of the fluorescence detection instrument of FIG. 6.
Figure 8:
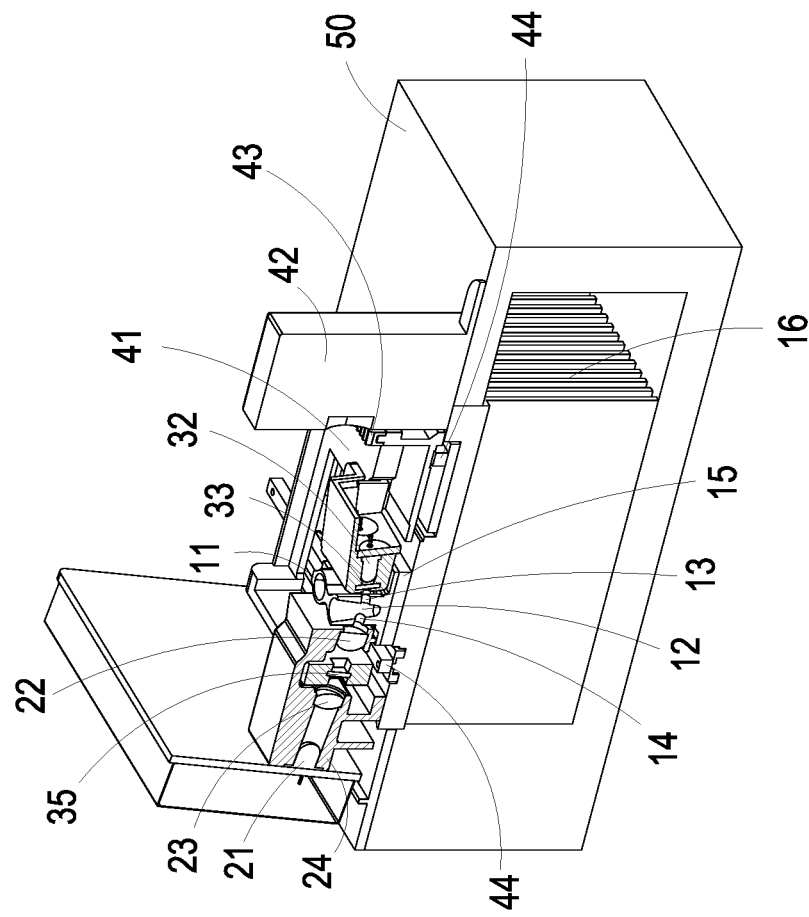
FIG. 8 shows a cross sectional view of the fluorescence detection instrument of FIG. 6.
Figure 9:
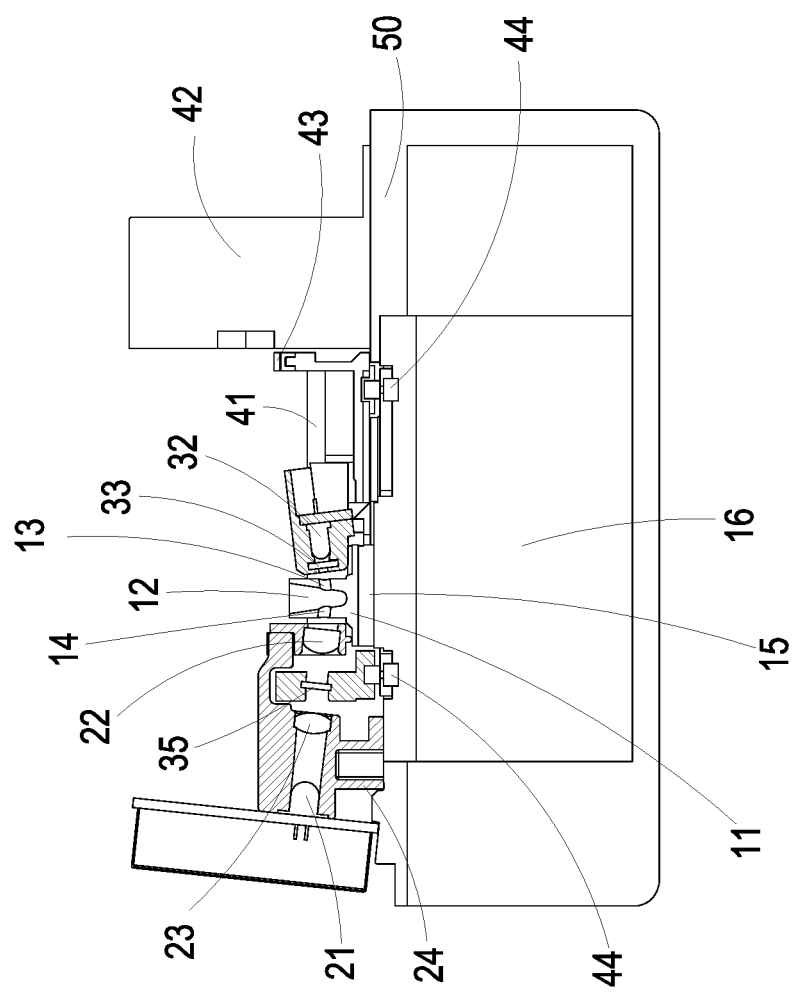
FIG. 9 shows a lateral view of FIG. 8.

FIG. 6 shows a schematic view of the fluorescence detection instrument according to another embodiment of the present invention, FIG. 7 shows an exploded view of the fluorescence detection instrument of FIG. 6, FIG. 8 shows a cross-sectional view of the fluorescence detection instrument of FIG. 6, and FIG. 9 shows a lateral view of FIG. 8. As shown in FIGS. 6 to 9, in the embodiment, the structures, elements and functions of the fluorescence detection instrument 1 are similar to those of the fluorescence detection instrument 1 of FIGS. 1 to 4, and are not repeatedly described herein. Different from the fluorescence detection instrument 1 of FIGS. 1 to 4, in the embodiment, the guiding rail module 44 includes for example two guiding rails disposed on the base 50 and located nearby two ends of the moveable support rack 41, respectively. It facilities the illumination module 30 constructed on the moveable support rack 41 to slide relative to the base 50 smoothly and stably. Certainly, the number and the type of the guiding rails of the guiding rail module 44 are not an essential feature to limit the embodiment of the present invention. It is adjustable according to the configuration of the gear module 43 and the actuator 42. It is noted that any actuator 42 adapted for changing the relative positions between the illumination module 30 and the heating module 10 are suitable in the embodiment of the present invention. In the embodiment, the actuator 42 includes for example but not limited to at least one of a rotary actuator driven by fluid or vacuum pressure, a piezoelectric (PZT) actuator, an electro-actuated polymer (EAP) actuator, and/or an electromagnetic motor.

In the embodiment, the illumination module 30 includes for example six light sources 32 and six first filters 33. The plural light sources 32 are disposed relative to the plural first filters 33, respectively and configured to illuminate six light beams for exciting the targeted fluorescent probe of the fluorescent reaction mixture (also called as PCR mixture) contained in the light-transmissive reaction container and generating the fluorescent light. In the embodiment, the plural light sources 32 includes for example but not limited to at least one of a single color LED, a laser diode, a mercury lamp and a halogen light bulb. Moreover, each of the plural light sources 32 emits light within a particular range of wavelengths in visible wavelengths, for example ranged from 480 nm to 500 nm at covering targeted excitation wavelengths. The light source 32 and the first filter 33 are configured to form a first optical axis A1. The light beam of the light source 32 is transmitted along the first optical axis A1. In the embodiment, six first optical axes A1 are formed. The plural first filters 33 include for example but not limited to single band pass filters. Moreover, each of the plural first filters 33 applied in the illumination module 30 is an excitation filter and only allows the light beam of the light source 32 falling within excitation bandwidth to pass therethrough. For preventing from the scattering light, the coating surface of the first filter 33 face to the heating module 10. The plural first filters 33 can be the same or different. Namely, the illumination module 30 can provide the plural light beams with the same color or different colors for multiplexing qPCR application. In the embodiment, the size of the first filter is 5 mm×5 mm×1 mm, but its size might change for different application. On the other hand, the illumination module 30 further includes a housing 34. The material of the housing 34 of the illumination module 30 may be for example black acrylonitrile butadiene styrene (ABS) for its low thermal conductivity, high thermal resistivity, and reduction of internal light scattering. Other kinds of black plastic materials with low reflectivity, or aluminum coated by black anodized coating possessing low reflectance and high absorptance are also applicable.

In the embodiment, the heating module 10 includes for example six heating holders 11 adapted for accommodating the light-transmissive reaction container (not shown) having the fluorescent reaction mixture with the targeted fluorescent probe, respectively. Each of the plural heating holders 11 further includes a heating chamber 12, a first optical aperture 13, and a second optical aperture 14. In each heating holder 11, the first optical aperture 13 and the second optical aperture 14 are communicated with each other through the heating chamber 12. Moreover, in each detection channel, the first optical aperture 13, the heating chamber 12, and the second optical aperture 14 are disposed linearly. The second optical aperture 14 faces to the detecting module 20. The first optical aperture 13 is adapted for matching with the light beam from one of the light sources 32 of the illumination module 30 to obtain at least one combination of the light source 32 and the heating holder 11 on the corresponding detection channel. In the embodiment, the diameter of the first optical aperture 13 is ranged from 1 mm to 2.5 mm, and the diameter of the second optical aperture 14 is ranged from 2 mm to 3 mm. Moreover, the heating holders 11 of the heating module 10 are made of copper, which is thermally conductive, and transfers heat uniformly in minutes to meet rapid thermal cycling requirement. Other thermally conductive material might be applied, such as aluminum or other thermal-conductive metals or materials etc. The plural heating holders 11 are arranged linearly and corresponding to the plural detection channels, respectively, for multiplexing sample detection. In the embodiment, the heating module 10 further includes a heater 15 and a heat sink 16. The heater 15 includes for example a thermoelectric cooling heater connected to the heating holders 11 for thermal cycling control. The heat sink 16 is further connected to the heater 15.

The detecting module 20 includes plural detectors 21 and plural optic sets of condensing optics 22 and imaging optics 23, wherein the plural detectors 21 are disposed relative to the plural optic sets of the condensing optics 22 and the imaging optics 23, respectively. The detector 21 and the set of the condensing optic 22 and the imaging optic 23 are disposed linearly and configured to form for example six second optical axes A2 along the detection channel. Each of the condensing optics 22 of the detecting module 20 is located nearby the heating module 10 for collecting the fluorescent light generated from the fluorescent reaction mixture and refracting to a uniformly distributed parallel beam. Each of the imaging optics 23 of the detecting module 20 is located nearby the corresponding detectors 21 for focusing the fluorescent light on the imaging plane of the corresponding detectors 21. A silicon photodiode can be chosen as the detector 21, but other types of detector, such as a photomultiplier tube (PMT), a charged-couple device (CCD), a complementary metal-oxide semiconductor (CMOS) or an avalanche photodiode (APD) could work on the detecting module 20 as well. In the embodiment, the illumination module 30 further includes plural second filters 35 as emission filters constructed on the moveable support rack 34 and located between the plural condensing optics 22 and the imaging optics 23. The second filters 35 may include single band pass filters and have the coating surface thereof to face to the condensing optics 22, respectively. In the embodiment, the size of the second filter 35 is for example 5 mm×5 mm×1 mm for each detection channel, but its size might change for different application. Moreover, the radius of curvature of the condensing optic 22 is for example 4 mm, and the plano surface thereof faces to the second optical aperture 14 of the heating module 10. The radius of curvature of the imaging optic 23 is for example 11 mm. The materials of the condensing optics 22 and the imaging optic 23 applied in the embodiment of the present invention include optical grade glass, but injection molded optical plastic, such as acrylic (PMMA), polycarbonate (PC), polystyrene or polyolefin, are also applicable. In the embodiment, the detecting module 20 further includes a fixed rack 24 fixed on the base 50. The plural detector 21, the plural condensing optics 22, and the plural image optics 23 are mounted and arranged in the fixed rack 24. Each detection channel includes the detector 21, the imaging optic 23, and the condensing optic 22 integrated together and disposed linearly on optical axis A2. It facilitates to reduce risk of misalignment of the detection channels. It is noted that the detecting module 20 designed in a sandwich type structure includes the condensing optics 22, the imaging optic 23, and the detector 21 and configured with the second filter 35 located between the condensing optics 22 and the imaging optic 23 in one detection channel. The plural second filters 35 of the illumination module 30 are mounted and accommodated within the moveable support rack 41 of the actuation module 40 to prevent the non-uniform illumination through the second filter 35. Moreover, the plural light sources 32, the plural first filters 33 and the plural second filters 35 of the illumination module 30 are integrated together and mounted within the moveable support rack 41 of the actuation module 40. It facilitates to reduce risk of misalignment during the operation of matching the light beams and the detection channel. In other embodiment, the second filter 35 can be integrated between the condensing optics 22 and the image optic 23 and embed in the fixed rack 24. The embodiment of the present invention is not limited thereto, and are not redundantly described herein.

On the other hand, the detecting module 20 further includes a photodiode amplifier (not shown) to convert electrical current output from the detector 21 in few nano ampere to voltage. The photodiode amplifier amplifies the signal for further data analysis and utilization. In an embodiment, the detecting module 20 further includes the electromagnetic (EMI) shielding and grounding structure (not shown) to cover the detector 21. The detector 21 might be influenced by the electromagnetic noise signals in the ambient environment because of its high sensitivity. The EMI shielding and grounding structure may be integrated in the fixed rack 24. The fixed rack 24 for accommodating the plural detectors 21, the plural condensing optics 22, and the plural imaging optics 23 may be made of black ABS (acrylonitrile butadiene styrene) material to avoid internal light reflection and scattering. Other black and machinable materials, such as polylactide (PLA), polycarbonate (PC), polyetheretherketone (PEEK), polyphenylene (PPE), and/or aluminum with black anodized coating are all applicable. The external surface of the fixed rack 24 is coated with metallic paint to insulate the EMI noise on the detector 21. Besides, the material of the fixed rack 24 could be aluminum coated with a dielectric black anodized layer. The black anodized coating may prevent the short circuit between positive and negative leads of the detector 21 and reduce the internal light scattering inside the detection channels, which is another source of noise signal.

In the embodiment, while the light source 32 is matched and aligned to the heating holder 11 on the corresponding detection channel, one combination of the light source 32, the first filter 33, the heating chamber 12, the condensing optic 22, the second filter 35, the imaging optic 23, and the detector 21 is matched in a linear arrangement, as shown in FIG. 5. The first optical axis A1 and the corresponding second optical axis A2 are crossed in the heating chamber 12 through the first optical aperture 13 and the second optical aperture 14 respectively. The light beam of the selected light source 32 illuminates the light-transmissive reaction container containing the fluorescent reaction mixture with the targeted fluorescent probes in the heating chamber 12 through the first optical aperture 13, and a generated fluorescent light is transmitted through the second optical aperture 14 along the corresponding detection channel. In an embodiment, while the first optical axis A1 is crossed with the corresponding second optical axis A2 in the heating chamber 12 through the first optical aperture 13 and the second optical aperture 14, the corresponding second optical axis A2 is tilted from the first optical axis A1 at an angle θ ranged from 2 degrees to 12 degrees. The signal to noise ratio (SNR) of the optical path design is more than 11. In an embodiment, while the corresponding second optical axis A2 is tilted from the first optical axis A1 at 7 degrees and the optical path design is improved, the signal to noise ratio (SNR) can be up to 347.

Figure 10A:
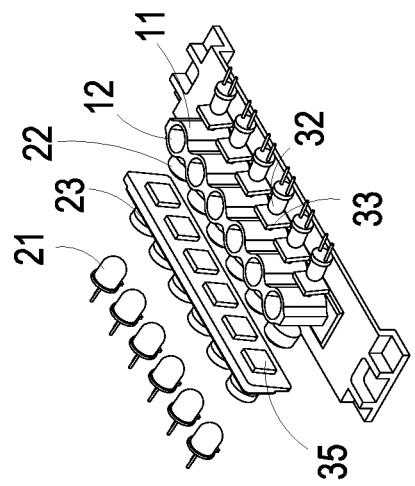
FIG. 10A shows a relative position of the illumination module, the heating module, and the detecting module of the fluorescence detection instrument of FIG. 1.
Figure 10B:
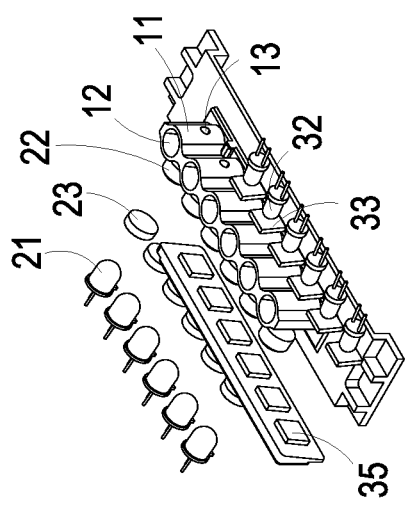
FIG. 10B shows another relative positions of the illumination module, the heating module, and the detecting module of the fluorescence detection instrument of FIG. 1.

FIGS. 10A and 10B show the relative positions of the illumination module, the heating module, and the detecting module of the fluorescence detection instrument of FIG. 1, respectively. As shown in FIGS. 1 to 5, 10A and 10B, while the illumination module 30 is driven by the actuation module 40 to change the position relative to the heating module 10 and the detecting module 20, at least one combination of the light source 32, the first filter 33, the heating chamber 12, the condensing optic 22, the second filter 35, the imaging optic 23, and the detector 21 is matched in a linear arrangement, as shown in FIG. 5. In FIG. 10A, there are four detection channels matched for performing qPCR detection. In FIG. 10B, there are six detection channels matched for performing qPCR detection. By changing positions of the illumination module 30, the fluorescence detection instrument 1 of the embodiment of the present invention could work on a batch of qPCR samples and achieve the multiplexing qPCR application.

Figure 11:
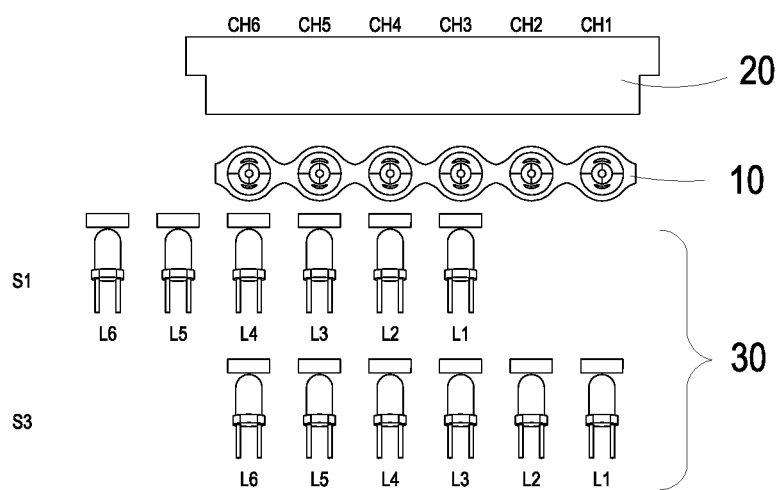
FIG. 11 show a first exemplary operation mechanism of the fluorescence detection instrument according to the embodiment of the present invention.

FIG. 11 shows a first exemplary operation mechanism of the fluorescence detection instrument according to the embodiment of the present invention. In the exemplary embodiment, the fluorescence detection instrument includes the similar structures, elements and functions as those of the foregoing embodiments in FIGS. 1 to 5, 10A and 10B, and are not repeatedly described herein. In the exemplary embodiment, the six light sources 32 and the six first filters 33 are configured to provide six light beams L1~L6 at the same color for exciting the targeted fluorescent probes of the fluorescent reaction mixtures. The operation mechanism of single color detection can be applied as shown in FIG. 11. There are six detection channels CH1~CH6. At an initial position S1, the light beams L1~L4 are matched to the detection channels CH3~CH6, respectively. While the illumination module 30 is moved to a detecting position S3, the light beams L1~L6 are matched to the detection channels CH1~CH6, respectively. Consequently, a batch of six samples placed on the detection channels CH1~CH6 may be illuminated by the light beams L1~L6 at single color and achieve the qPCR detection efficiently.

Figure 12:
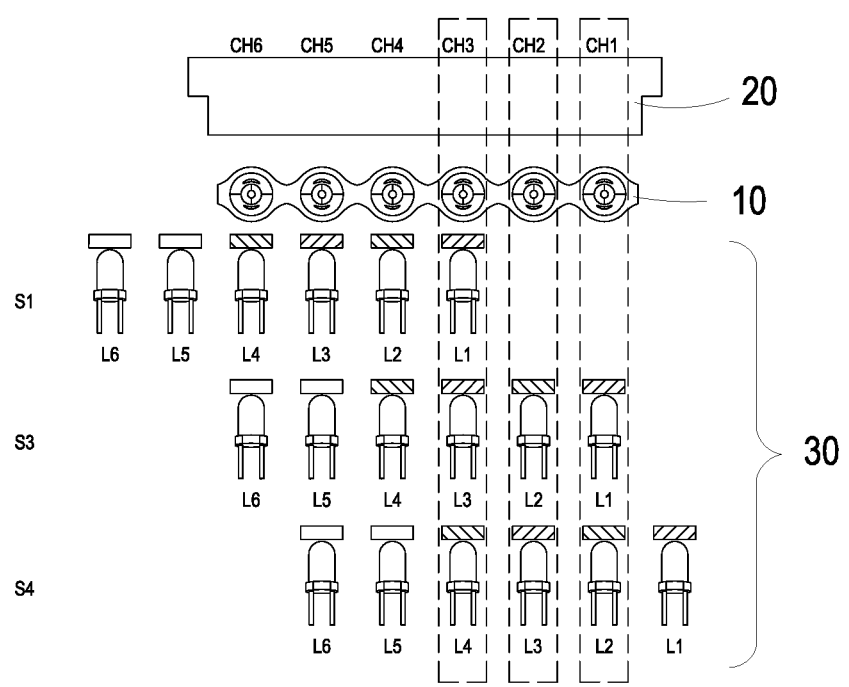
FIG. 12 show a second exemplary operation mechanism of the fluorescence detection instrument according to the embodiment of the present invention.

FIG. 12 shows a second exemplary operation mechanism of the fluorescence detection instrument according to the embodiment of the present invention. In the exemplary embodiment, the fluorescence detection instrument includes the similar structures, elements and functions as those of the foregoing embodiment in FIGS. 1 to 5, 10A and 10B, and are not repeatedly described herein. In the exemplary embodiment, the six light sources 32 and the six first filters 33 are configured to provide six light beams L1~L6 with dual color for exciting the targeted fluorescent probes of the fluorescent reaction mixtures. The light beams L1 and L3 may be for example the same red color, and the light beams L2 and L4 may be for example the same blue color. For example, three samples are placed on the detection channels CH1~CH3. The operation mechanism of dual color detection may be applied as shown in FIG. 12. There are six detection channels CH1~CH6. At an initial position S1, the light beams L1~L4 are matched to the detection channels CH3~CH6, respectively. Firstly, the illumination module 30 is moved to a detecting position S3, and the light beams L1~L3 are matched to the detection channels CH1~CH3, respectively. Then, the illumination module 30 is moved to a detecting position S4, and the light beams L2~L4 are matched to the detection channels CH1~CH3. Consequently, a batch of three samples placed on the detection channels CH1~CH3 can be illuminated by the light beams L1~L4 at dual color and achieve the qPCR detection efficiently.

Figure 13:
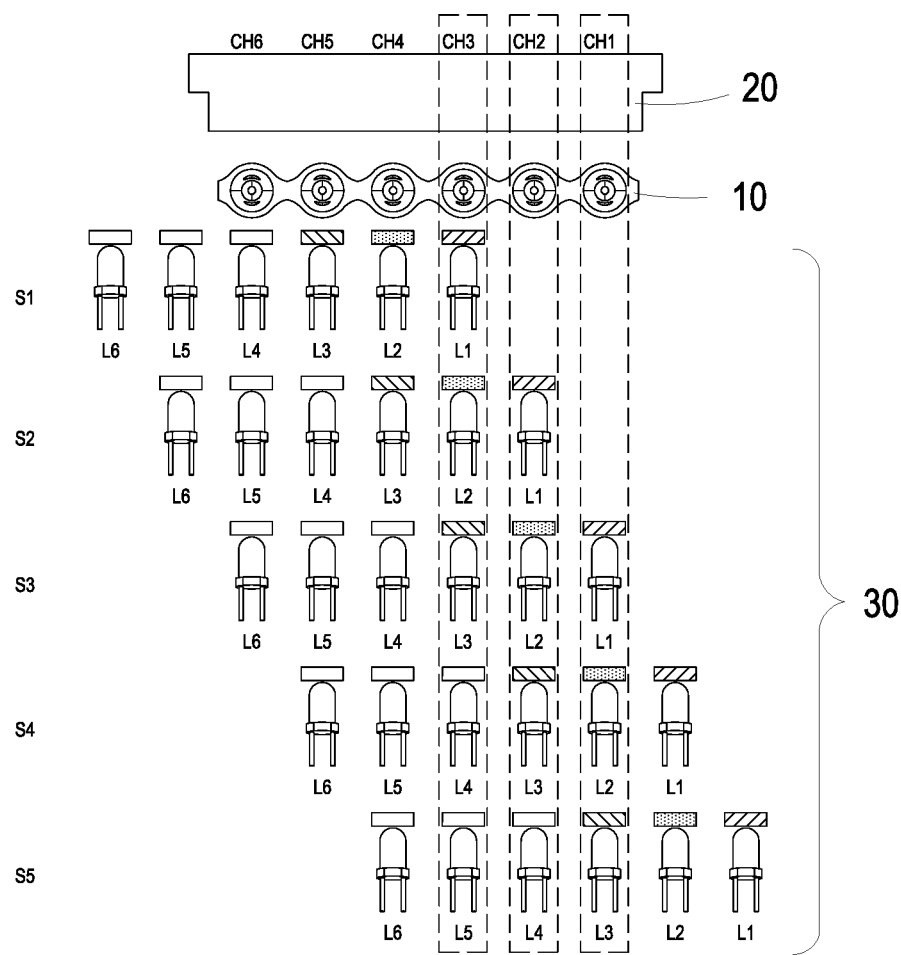
FIG. 13 shows a third exemplary operation mechanism of the fluorescence detection instrument according to the embodiment of the present invention.

FIG. 13 shows a third exemplary operation mechanism of the fluorescence detection instrument according to the embodiment of the present invention. In the exemplary embodiment, the fluorescence detection instrument includes the similar structures, elements and functions as those of the foregoing embodiment in FIGS. 1 to 5, 10A and 10B, and are not repeatedly described herein. In the exemplary embodiment, the six light sources 32 and the six first filters 33 are configured to provide six light beams L1~L6 with triple color for exciting the targeted fluorescent probes of the fluorescent reaction mixtures. The light beam L1 may be for example the red color, the light beam L2 may be for example the blue color, and the light beam L3 may be for example the yellow color. Three samples are placed on the detection channels CH1~CH3. The operation mechanism of triple color detection can be applied as shown in FIG. 13. There are six detection channels CH1~CH6. At an initial position S1, the light beams L1~L3 are matched to the detection channels CH3~CH5, respectively. Meanwhile, the light beam L1 is matched to the detection channel CH3, and the triple color detection is started. Then, the illumination module 30 is moved to detecting positions S2, S3, S4 and S5 in order, and each of the detection channels CH1~CH3 can be illuminated by the light beams L1~L3 step by step. Consequently, a batch of three samples placed on the detection channels CH1~CH3 can be illuminated by the light beams L1~L3 at triple color and achieve the qPCR detection efficiently.

Figure 14A:
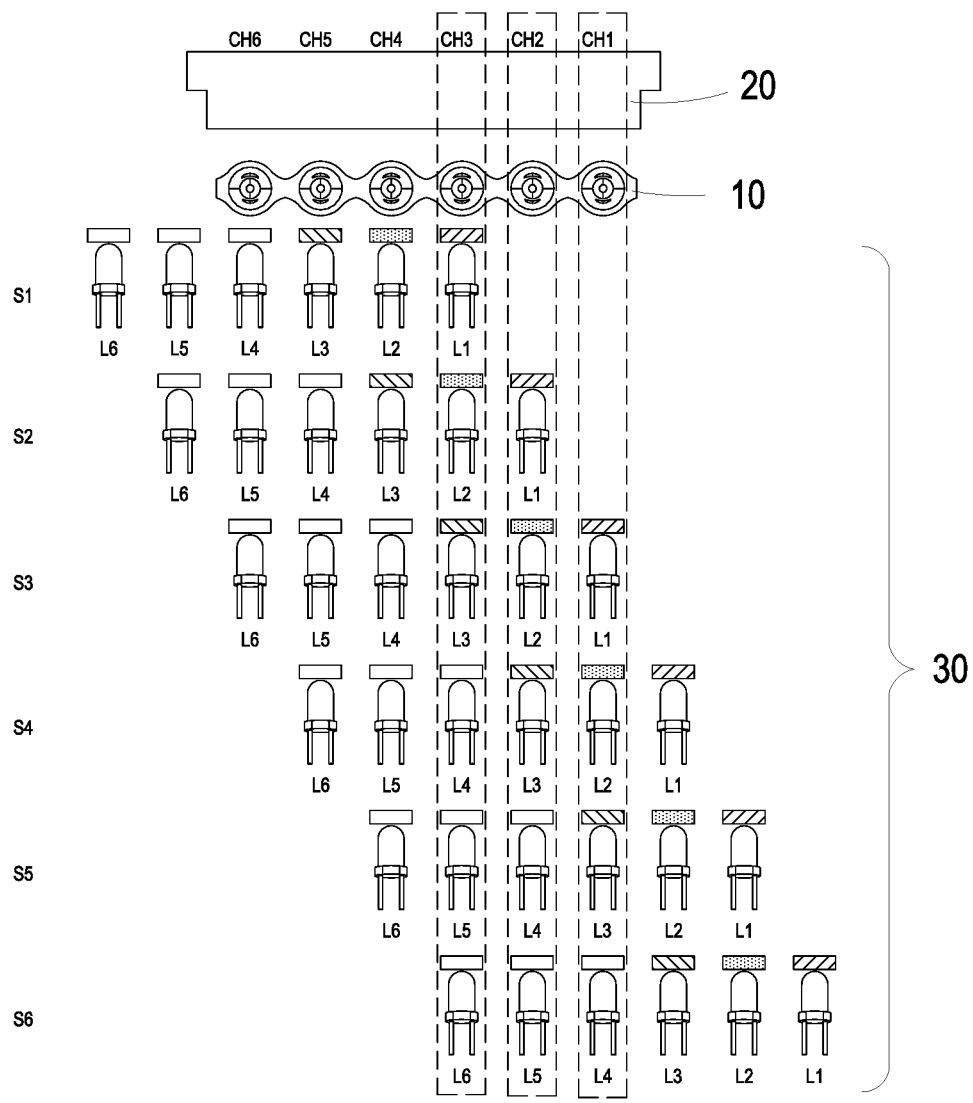
FIG. 14A shows a fourth operation mechanism of the fluorescence detection instrument according to the embodiment of the present invention.
Figure 14B:
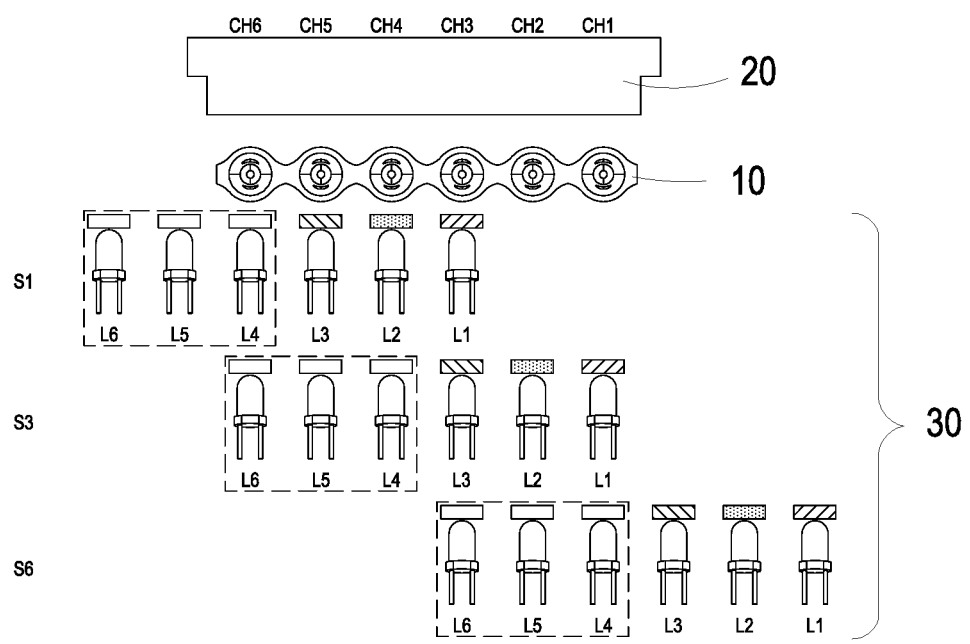
FIG. 14B shows a fifth exemplary operation mechanism of the fluorescence detection instrument according to the embodiment of the present invention.

FIGS. 14A and 14B show a fourth and fifth exemplary operation mechanisms of the fluorescence detection instrument according to the embodiment of the present invention, respectively. In the exemplary embodiment, the fluorescence detection instrument includes the similar structures, elements and functions as those of the foregoing embodiment in FIGS. 1 to 5, 10A and 10B, and are not repeatedly described herein. For integrating versatile functions in the fluorescence detection instrument 1, the six light sources 32 and the six first filters 33 are configured to provide six light beams L1~L6 with single color and quad color for exciting the targeted fluorescent probe(s) of the fluorescent reaction mixture. The light beam L1 may be for example the red color, the light beam L2 may be for example the yellow color, the light beam L3 may be for example the green color, and the light beams L4~L6 may be for example the same blue. The operation mechanisms of single color and multi-color detection may be applied simultaneously in the fluorescence detection instrument 1 of the embodiment of the present invention. The operation mechanism of quad color detection may be applied as shown in FIG. 14A and the operation mechanism of the single color detection may be applied as shown in FIG. 14B. Certainly, the fluorescence detection instrument 1 has the flexibility of performing single color detection to quad color detection efficiently, and are not redundantly described herein. In other embodiment, the number of the light sources 32 for matching to the detection channels may be more than the number of the detection channels. For providing versatile functions of single color detection to multi-color detection, the illumination module 30 may include at least two adjacent light sources providing the same color of light and at least two adjacent light sources providing the different colors of light. In one embodiment, the at least two adjacent light source 32 with the same color, such as the light beams L4~L6 of FIGS. 14A and 14B, are disposed from the far end of the arrangement of the light beams L1~L6 to increase the efficiency of versatile detection. In one embodiment, the at least two adjacent light source 32 with the same color, such as the light beams L5~L6 of FIGS. 14A and 14B, are disposed at an end of the arrangement of the light beams L1~L6.

Moreover, in the embodiment, the fluorescent probes, FITC and Cy5 are utilized, wherein FITC can be excited by blue light and Cy5 can be excited by red light. A light-transmissive reaction container placed on the detection channel CH1 is filled with the nucleic acids binding with the targeted fluorescent probes. According to the experiment results, there is low crosstalk effect between the two targeted fluorescent probes, and the related SNR of FITC and Cy5 at different concentrations are shown in the following Table 1. While the concentration is increased, the SNR is increased.

TABLE 1

|  | FITC | Cy5 |
| --- | --- | --- |
| SNR_320 nM | 24.46 | 25.15 |
| SNR_20 nM | 2.31 | 2.70 |

In conclusion, the embodiments of the present invention provides the fluorescence detection instrument integrating with switchable illumination module for multiplexing qPCR application with affordable cost. The well-designed optical structure miniaturizes the size and reduces the cost of the illumination module and the detecting module, but still provides promising performance whose signal to noise ratio (SNR) could be up to 347. The overall dimension of the system is about 150 mm×110 mm×38 mm. The components and structure of the fluorescence detection instrument contributes the compactness of this optical system. The arrangement of the switchable illumination module provides the efficient light sources with versatile functions. The operation mechanism of single color detection and multi-color detection may be applied simultaneously in the fluorescence detection instrument of the embodiments of the present invention. Different from the existing technologies applied on multi-color PCR systems, such as filter wheel, rotational LED and detection wheel, or translational detection structure, etc. The design of the embodiments of the present invention adopts fixed detector and optic sets. The integration of light source and filter sets reduces the misalignment issues during color switching. Moreover, the arrangements of light sources and filter sets with motional control enable the hybrid of single color and multi-color detection. The arrangements of light sources with excitation and emission filter sets are versatile. The fluorescence detection instrument is compact, but still flexible to meet requirements of multiplexing qPCR application.

The foregoing sets out a number of features of the embodiments, so that the ordinary skill in the art may more preferably be understood that aspects of the present invention. Ordinary skill in the art will appreciate that the present invention may be intended to use as a basis for designing or modifying other structures and operations to achieve the same purposes described herein, embodiments and/or embodiments described herein reach embodiment the same advantages. Ordinary skill in the art should also recognize that these equivalent constructions do not depart from the spirit and scope of the invention, and various changes thereof may be made without departing from the spirit and scope of the invention, the substituted or alternatively.

What is claimed is:

1. A fluorescence detection instrument comprising:
a base;
a heating module disposed on the base and comprising plural heating holders, wherein each of the plural heating holders is adapted to accommodate a light-transmissive reaction container adapted to contain a fluorescent reaction mixture with at least one targeted fluorescent probe, respectively;
a detecting module disposed on the base and configured with the heating module to form plural detection channels, wherein the plural heating holders are located on the plural detection channels, respectively;
an illumination module; and
an actuation module disposed on the base, connected with the illumination module and adapted to drive the illumination module to move to at least one predetermined position to selectively match at least one combination of the heating holder on the corresponding detection channel.

2. The fluorescence detection instrument according to claim 1, wherein the illumination module comprises plural light sources and plural first filters, wherein the plural light sources are disposed relative to the plural first filters, respectively, and the light source and the first filter are configured to form a first optical axis.

3. The fluorescence detection instrument according to claim 2, wherein the light source comprises at least one of a single color LED, a laser diode, a mercury lamp, and a halogen light bulb.

4. The fluorescence detection instrument according to claim 2, wherein the plural light sources comprise at least two adjacent light sources adapted to provide the same color of light and at least two adjacent light sources adapted to provide the different colors of light, wherein the at least two adjacent light sources adapted to provide the same color of light are disposed at an end of the arrangement of the plural light sources.

5. The fluorescence detection instrument according to claim 2, wherein the illumination module comprises plural second filters relative to the plural first filters respectively, wherein the plural second filters are located between the detecting module and the heating module.

6. The fluorescence detection instrument according to claim 5, wherein the plural first filters and the plural second filters comprise single band pass filters.

7. The fluorescence detection instrument according to claim 5, wherein the plural first filters comprise excitation filters, and the plural second filter comprise emission filters.

8. The fluorescence detection instrument according to claim 2, wherein the detecting module comprises plural detectors and plural optic sets, wherein the plural detectors are disposed relative to the plural optic sets respectively, and the detector and the corresponding plural optic set are configured to form a second optical axis along the detection channel.

9. The fluorescence detection instrument according to claim 8, wherein the detector comprises at least one of a silicon photodiode, a photomultiplier tube, a charged-couple device, a complementary metal-oxide semiconductor, and an avalanche photodiode.

10. The fluorescence detection instrument according to claim 8, wherein each of the plural optic sets comprises at least one condensing optic located nearby the heating module and at least one imaging optic located nearby the corresponding detector.

11. The fluorescence detection instrument according to claim 10, wherein each of the plural optic sets comprises an emission filter disposed between the condensing optic and the imaging optic.

12. The fluorescence detection instrument according to claim 8, wherein each of the plural heating holders comprises a heating chamber, a first optical aperture, and a second optical aperture, wherein the first optical aperture and the second optical aperture are communicated with each other through the heating chamber, and the second optical aperture is located at the corresponding second optical axis.

13. The fluorescence detection instrument according to claim 12, wherein the diameter of the first optical aperture is ranged from 1 mm to 2.5 mm, and the diameter of the second optical aperture is ranged from 2 mm to 3 mm.

14. The fluorescence detection instrument according to claim 12, wherein while the illumination module is matched and aligned to the heating holder on the corresponding detection channel, the first optical axis and the corresponding second optical axis are crossed in the heating chamber through the first optical aperture and the second optical aperture respectively.

15. The fluorescence detection instrument according to claim 12, wherein while the first optical axis and the corresponding second optical axis are crossed in the heating chamber through the first optical aperture and the second optical aperture respectively, the corresponding second optical axis is tilted from the first optical axis at an angle, wherein the angle is ranged from 2 degrees to 12 degrees.

16. The fluorescence detection instrument according to claim 1, wherein the heating module further comprises a heater connected with the plural heating holders.

17. The fluorescence detection instrument according to claim 16, wherein the heater comprises a thermoelectric cooling heater for thermal cycling control.

18. The fluorescence detection instrument according to claim 16, wherein the heating module further comprises a heat sink connected to the heater.

19. The fluorescence detection instrument according to claim 1, wherein the actuation module comprises at least one actuator, wherein the actuator comprises at least one of a rotary actuator driven by fluid or vacuum pressure, a piezoelectric actuator, an electro-actuated polymer actuator, and an electromagnetic motor.

20. The fluorescence detection instrument according to claim 19, wherein the actuation module comprises a moveable support rack, wherein the illumination module is disposed on the moveable support rack and connected to the at least one actuator, wherein the at least one actuator is configured to drive the movable support rack and move the illumination module to selectively match the at least one combination of the heating holder on the corresponding detection channel.

21. The fluorescence detection instrument according to claim 20, wherein the actuation module comprises a gear module and at least one guiding rail module, wherein the gear module is disposed between and connected with the actuator and the movable support rack, and the at least one guiding rail module is disposed between and connected with the moveable support rack and the base.

22. The fluorescence detection instrument according to claim 1, further comprising a moveable support rack, wherein the illumination module is disposed on the moveable support rack and connected to the actuation module, wherein the actuation module is configured to drive the movable support rack and move the illumination module to selectively match the at least one combination of the heating holder on the corresponding detection channel.

23. The fluorescence detection instrument according to claim 1, wherein the number of the combinations of the illumination module and the heating holder on the corresponding detection channel is less than the total number of the plural detection channels.

* * * * *